US008300905B2

(12) United States Patent
Jabri

(10) Patent No.: US 8,300,905 B2
(45) Date of Patent: Oct. 30, 2012

(54) ADAPTIVE IMAGE PROCESSING AND DISPLAY FOR DIGITAL AND COMPUTED RADIOGRAPHY IMAGES

(75) Inventor: Kadri N. Jabri, Waukesha, WI (US)

(73) Assignee: General Electric Company, Schenectady, NY (US)

(*) Notice: Subject to any disclaimer, the term of this patent is extended or adjusted under 35 U.S.C. 154(b) by 1377 days.

(21) Appl. No.: 11/283,212

(22) Filed: Nov. 18, 2005

(65) Prior Publication Data
US 2007/0116348 A1 May 24, 2007

(51) Int. Cl.
*G06K 9/00* (2006.01)
(52) U.S. Cl. ............. 382/128; 355/35; 396/65; 399/51; 398/92; 398/96; 600/1
(58) Field of Classification Search .................... 382/132
See application file for complete search history.

(56) References Cited

U.S. PATENT DOCUMENTS

| | | | | |
|---|---|---|---|---|
| 5,955,738 | A * | 9/1999 | Manabe et al. | 250/492.22 |
| 6,125,166 | A | 9/2000 | Takeo | |
| 6,795,572 | B1 * | 9/2004 | Matsuno | 382/132 |
| 6,816,572 | B2 | 11/2004 | Jabri et al. | |
| 7,110,495 | B2 | 9/2006 | Tamegai | |
| 7,260,255 | B2 * | 8/2007 | Polichar et al. | 382/132 |
| 7,386,158 | B2 | 6/2008 | Yamada | |
| 2001/0033681 | A1 * | 10/2001 | Wang | 382/132 |
| 2002/0054697 | A1 * | 5/2002 | Wang | 382/128 |
| 2002/0196418 | A1 * | 12/2002 | Hagiwara et al. | 355/67 |
| 2003/0094582 | A1 * | 5/2003 | Weiss et al. | 250/492.3 |
| 2003/0095192 | A1 * | 5/2003 | Horiuchi | 348/222.1 |
| 2003/0138742 | A1 * | 7/2003 | Irie et al. | 430/396 |
| 2003/0152258 | A1 * | 8/2003 | Jabri et al. | 382/132 |
| 2003/0190067 | A1 * | 10/2003 | Tsujii | 382/132 |
| 2004/0028182 | A1 * | 2/2004 | Tamegai | 378/98.7 |
| 2004/0101086 | A1 * | 5/2004 | Sabol et al. | 378/4 |
| 2004/0132854 | A1 * | 7/2004 | Du Plessis et al. | 522/114 |
| 2006/0039238 | A1 * | 2/2006 | Mandal et al. | 367/31 |
| 2006/0039532 | A1 * | 2/2006 | Wu et al. | 378/62 |
| 2006/0104496 | A1 * | 5/2006 | Arenson et al. | 382/132 |

FOREIGN PATENT DOCUMENTS

| | | |
|---|---|---|
| EP | 1223553 A2 | 7/2002 |
| EP | 1388741 A2 | 2/2004 |
| JP | 01-054341 A | 3/1989 |
| JP | 2000-060834 A | 2/2000 |

(Continued)

OTHER PUBLICATIONS

Nicholson et al., "Skin Sparing in Interventional Radiology: the Effect of Copper Filtration," 2000, The British Journal of Radiology, vol. 73 pp. 36-42.*

(Continued)

*Primary Examiner* — John Lee
(74) *Attorney, Agent, or Firm* — McAndrews, Held & Malloy, Ltd.; William Baxter

(57) ABSTRACT

The presently described technology provides a method for adaptive image processing. The image processing method includes determining an entrance exposure of an object, determining an exit exposure of the object, and determining one or more image processing parameters based at least in part on the entrance and exit exposures. The presently described technology also provides a method for adaptive image display. The image display method includes determining an entrance exposure of an object, determining an exit exposure of the object, and displaying an attenuation map based at least in part on the entrance and exit exposures.

23 Claims, 3 Drawing Sheets

FOREIGN PATENT DOCUMENTS

| | | |
|---|---|---|
| JP | 2002-024822 A | 1/2002 |
| JP | 2002-133410 A | 5/2002 |
| JP | 2004-069441 A | 3/2004 |

OTHER PUBLICATIONS

Japan Patent Office—Office Action Application No. 2006-324327 (2 Pages) Jan. 30, 2012.

Japanese Office Action for JP Application No. 2006-324327, dated Jul. 3, 2012, (2 pages), This will not be considered, A translation is requested.

Japanese Office Action for JP Application No. 2006-324327, dated Jul. 3, 2012, (with unofficial English translation) (4 pages).

* cited by examiner

ADAPTIVE IMAGE PROCESSING AND DISPLAY FOR DIGITAL AND COMPUTED RADIOGRAPHY IMAGES

BACKGROUND OF THE INVENTION

The presently described technology relates generally to image processing and display for digital images. More specifically, the presently described technology relates to adaptive image processing and display for digital and computed radiography images.

X-ray imaging has long been an accepted medical diagnostic tool. X-ray imaging systems are commonly used to capture, as examples, thoracic, cervical, spinal, cranial, and abdominal images that often include information necessary for a doctor to make an accurate diagnosis. X-ray imaging systems typically include an x-ray source and an x-ray sensor. When having a thoracic x-ray image taken, for example, a patient stands with his or her chest against the x-ray source at an appropriate height. X-rays produced by the source travel through the patient's chest, and the x-ray sensor then detects the x-ray energy generated by the source and attenuated to various degrees by different parts of the body. An associated control system obtains the detected x-ray energy from the x-ray sensor and prepares a corresponding diagnostic image on a display.

The diagnostic image is typically of inconsistent quality as initially scanned. For example, the raw image of a small or thin patient is typically high contrast or dark compared to the raw image of a large or thick patient, which is typically low contrast or light. Inconsistent image quality makes it difficult for doctors, technicians, or other medical providers to read and interpret. Furthermore, as a result of the inconsistent quality of images, doctors, technicians, and other medical providers may misdiagnose medical conditions, thereby compromising the health and safety of their patients.

The quality of digital images, such as digital radiography (DR) images or computed radiography (CR) images, is typically improved or enhanced by image processing techniques, such as detail enhancement, dynamic range compression and/or management, scatter reduction, decomposition and/or subtraction (dual energy only), and display window determination, for example. Image processing techniques typically include image processing parameters, such as spatial-domain filtering kernel sizes and weighting coefficients, frequency-domain filtering thresholds, log-subtraction parameters (dual energy only), display window-level/center adjustment parameters, and display window-width adjustment parameters.

One technique for improving image quality is to manually select or adjust an appropriate image processing parameter based on an estimation of patient size or thickness by examination and/or measurement of the patient. For example, an operator or technician typically estimates patient size or thickness by visually examining the patient. Alternatively, for example, an operator or technician may estimate patient size or thickness by measuring the patient. More particularly, the operator or technician may measure the patient with a measuring device, such as a ruler or a tape measure, for example. The estimation of patient size or thickness typically include classifications, such as small, medium, or large, for example, wherein each classification corresponds to a pre-determined range of patient sizes or thicknesses. The operator or technician then manually adjusts or selects an appropriate image processing parameter based on the estimation of patient size or thickness.

There are several disadvantages to improving image quality by manually selecting or adjusting an appropriate image processing parameter based on an estimation of patient size or thickness by examination or measurement. First, manually selecting or adjusting an image processing parameter based on an estimation of patient size or thickness, whether by visual examination or measurement, for example, is not accurate. An operator or technician could easily make a mistake, either in estimating patient size or thickness or in selecting or adjusting an appropriate image processing parameter. Additionally, a broad classification, such as small, medium, or large, for example, typically includes a wide range of patient sizes or thicknesses. Consequently, an operator or technician could easily select the same image processing parameter for two patients of vastly different sizes or thicknesses, which would not be appropriate. Furthermore, the anatomy of an individual patient typically varies in size or thickness. Therefore, a single image processing parameter may not be appropriate even for an individual patient.

Second, manually selecting or adjusting an image processing parameter based on an estimation of patient size or thickness, whether by examination or measurement, for example, is not automatic. In order to be profitable, a hospital or clinic must examine a certain number of patients. Manually examining or measuring each patient prior to imaging takes more time, thereby limiting the number of patients that can be imaged in a given time period. Consequently, manually estimating patient sizes or thicknesses and manually selecting or adjusting image processing parameters not only wastes time, but it also is not cost effective.

Another technique for improving image quality is to manually select or adjust an appropriate image processing parameter based on an estimation of patient size or thickness with automatic exposure control ("AEC"). Image acquisition and patient exposure are typically controlled manually. For example, with manual exposure control, an operator or technician sets exposure peak voltage (kVp), current (mA), and duration (msec). The image acquisition and patient exposure end when the time expires.

Alternatively, image acquisition and patient exposure may be controlled automatically. For example, with automatic exposure control, an operator or technician sets the exposure peak voltage (kVp) and current (mA), but the exposure duration (msec) is determined by an AEC device. More particularly, the AEC device detects exposure energy after going through the patient or imaged object. The image acquisition and patient exposure end when the exposure level reaches an appropriate limit.

The exposure duration or time typically varies depending on the patient or object being imaged. For example, thicker patients or objects typically take longer to image than thinner patients or objects. Consequently, an operator or technician typically estimates patient size or thickness based on the exposure duration or time determined with automatic exposure control and then manually selects or adjusts an appropriate image processing parameter, such as small, medium, or large, for example.

There are several disadvantages to improving image quality by manually selecting or adjusting an appropriate image processing parameter based on an estimation of patient size or thickness with AEC. Manually selecting or adjusting an appropriate image processing parameter based on an estimation of patient size or thickness by AEC is not accurate. The locations or positions of the sensing regions of the AEC device are typically fixed within the imaging system. Therefore, if the patient or selected anatomy of the patient is not properly positioned and aligned with the sensing regions of the AEC device, then the exposure duration, as determined by the AEC device, and thus, the corresponding estimate of patient size or thickness may not be accurate. Additionally, the coverage of the AEC device is typically limited. More particularly, the AEC device does not necessarily cover the entire patient or anatomy to be imaged. In other words, the image or scan area is larger than that of the AEC device. Consequently, the exposure duration determined by the AEC device, and thus, the corresponding estimate of patient size may not be accurate.

Additionally, manually selecting or adjusting an image processing parameter based on an estimation of patient size or thickness with AEC may not be automatic. Although the AEC device automatically determines the exposure duration, the operator or technician typically manually estimates the patient size or thickness based on the exposure duration. Additionally, the operator or technician typically manually selects or adjusts the image processing parameter based on the estimation of patient size or thickness. As previously described, in order to be profitable, a hospital or clinic must examine a certain number of patients. Manually estimating the patient size or thickness and manually selecting or adjusting the image processing parameter requires additional time, thereby limiting the number of patients that can be imaged in a given time period. Consequently, manually estimating patient sizes or thicknesses and manually selecting or adjusting image processing parameters not only wastes time, but also increases cost.

Image processing parameters may also be selected or adjusted automatically based on AEC. However, as described above, accuracy and coverage are still of concern, even with automatic selection or adjustment of image processing parameters based on AEC.

Thus, there is a need for improving image quality in an imaging system. More particularly, there is a need for accurately and automatically determining image processing parameters in an imaging system based on properties of the imaged object or patient.

BRIEF DESCRIPTION OF THE INVENTION

The presently described technology provides a method for adaptive image processing. The adaptive image processing method includes determining an entrance exposure of an imaged object, determining an exit exposure of the image object, and determining one or more image processing parameters based at least in part on the entrance and exit exposures.

The presently described technology also provides a computer-readable storage medium including a set of instructions for a computer. The set of instructions includes determining an entrance dose of an imaged object, determining an exit dose of the imaged object, and determining one or more image processing parameters based at least in part on said entrance and exit doses.

The presently described technology also provides an imaging system for adaptive image processing. The imaging system includes an image processor. The image processor determines an entrance exposure of an image object based at least in part on energy transmitted by an energy source, an exit exposure of the imaged object based at least in part on energy received by an energy detector, and one or more image processing parameters based at least in part on the object entrance and exit exposures.

The presently described technology also provides a method for adaptive image display. The adaptive image display method includes determining an entrance exposure of an imaged object, determining an exit exposure of the imaged object, and displaying an attenuation map based at least in part on said entrance and exit exposures.

Figure 1:
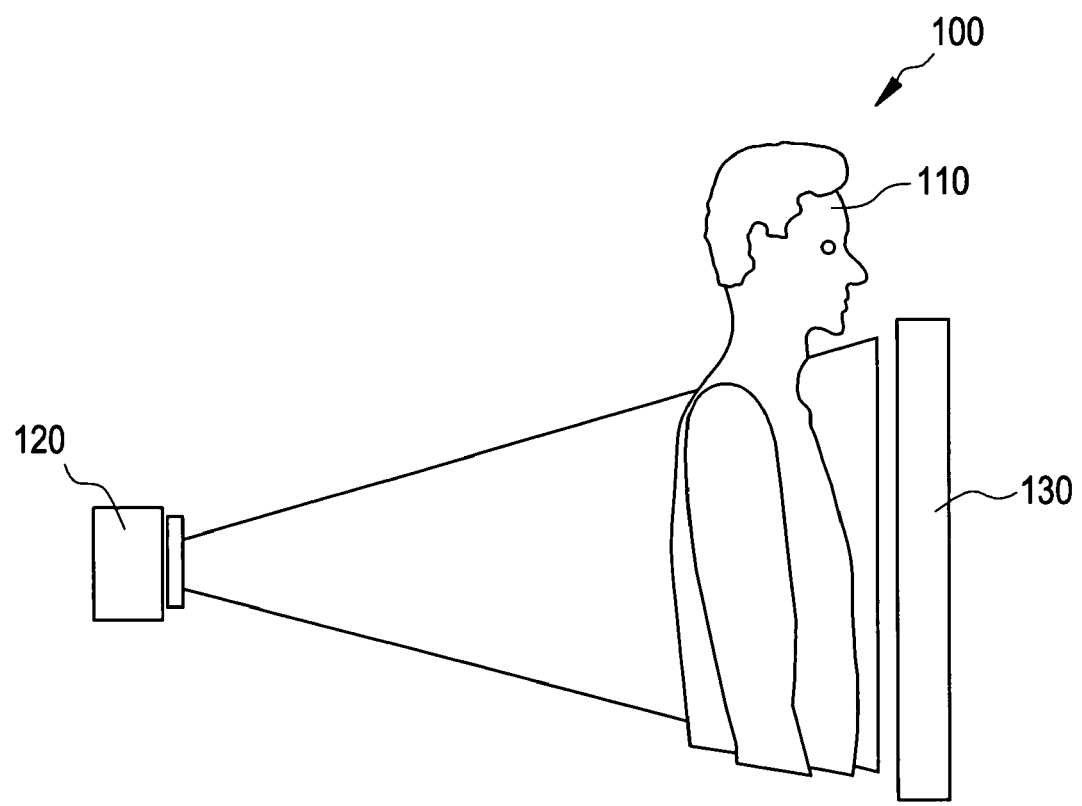
FIG. 1 illustrates an imaging system for adaptive image processing and/or display, according to at least one embodiment of the presently described technology.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the presently described technology is not limited to the arrangements and instrumentality shown in the attached drawings.

DETAILED DESCRIPTION OF THE INVENTION

FIG. 1 illustrates an imaging system 100 for adaptive image processing and/or display, according to at least one embodiment of the presently described technology. The imaging system 100 includes an object 110, an energy source 120, and an energy sensor 130. The imaging system 100 may also include an image processor 140 (not shown) and an image display 150 (not shown). The sensor or detector 130 may include a plurality of detector elements (not shown).

The components of the imaging system 100 may be implemented in software, hardware, and/or firmware, for example. The components of the imaging system 100 may be implanted separately and/or integrated in various forms, for example.

The object 110, such as a patient or selected area or anatomy of the patient, may be positioned or located in the imaging system 100. More particularly, the object 110 may be positioned or located between the energy source 120 and the energy sensor 130. The energy source 120 produces energy or radiation, such as x-rays, for example. The energy or radiation travels from the energy source 120, through the object 110, and into the energy sensor or detector 130. The detector 130 converts the energy or radiation into a raw image. More particularly, the detector elements convert the energy or radiation into pixels of the raw image.

The raw image may be shown on the image display 150. However, as described above, the raw image may be of poor quality. For example, the raw image of a small or thin patient may be high contrast or dark compared to the raw image of a large or thick patient, which may be low contrast or light.

Alternatively, the raw image may be adjusted by the image processor 140 or other such processors prior to being shown on the image display 150. Image processing parameters, such as spatial-domain filtering kernel sizes and weighting coefficients, frequency-domain filtering thresholds, log-subtraction parameters (dual energy only), display window-level/center adjustment parameters, and display window-width adjustment parameters, may be selected or adjusted to improve or enhance the quality of the raw or acquired image. The image quality of the processed image may also be inconsistent, as described above. However, the image quality of the processing image may be further improved or enhanced based on the method 200 of FIG. 2, as described below.

The image processor 140 may include one or more image processors. More particularly, multiple image processors may be included in the imaging system 100, each image processor dedicated to one or more functions of the imaging system. For example, a first processor may perform functions related to determining an entrance and exit exposure or dose, a second processor may perform functions related to determining image process parameters based on the entrance and exit exposures, and a third processor may perform functions related to displaying an attenuation value or map based on the entrance and exit exposures. These functions are described in more detail below. Alternatively, one image processor 140 may perform all of the image processing functions. The image processor 140 may also be included in one or more imaging systems.

The image processor 140 or other such processors may be in communication with the energy source 120 and/or the energy sensor 130. More particularly, the image processor 140 may be in communication with the energy source 120 to obtain information related to the source 120, such as geometric and/or technique parameters of the imaging system, for example. Additionally, the image processor 140 may be in communication with the energy sensor 130 to obtain information related to the sensor 130, such as the raw or acquired image, for example.

The attenuation of the object 110 may be determined in the direction of imaging (i.e., the direction of energy or radiation flow between the energy source 120 and the energy detector 130, for example. Using analytical methods, the size or thickness of the object 110 may be deduced from the object attenuation and the geometric and/or technique parameters of the imaging system. Analytical methods may include analytical modeling, such as modeling based on attenuation formulas or attenuation lookup tables, or numerical modeling, such as modeling based on Monte Carlo simulations. Additionally, for example, if the imaging system 100 includes multiple energy sources 120 and/or multiple energy detectors 130, or if the imaging system 100 includes a moving energy source 120 and/or a moving energy detector 130, the object size or thickness may be determined in multiple directions. An example of such an imaging system 100 includes a three-dimensional x-ray imaging system. Using limited-angle reconstruction algorithms, the attenuation of an object may be determined at multiple planes or slices parallel to the detector. This effectively creates a three dimensional attenuation map of the object. The attenuation of the object 110 may be determined by the imaging system 100 as follows.

Figure 2:
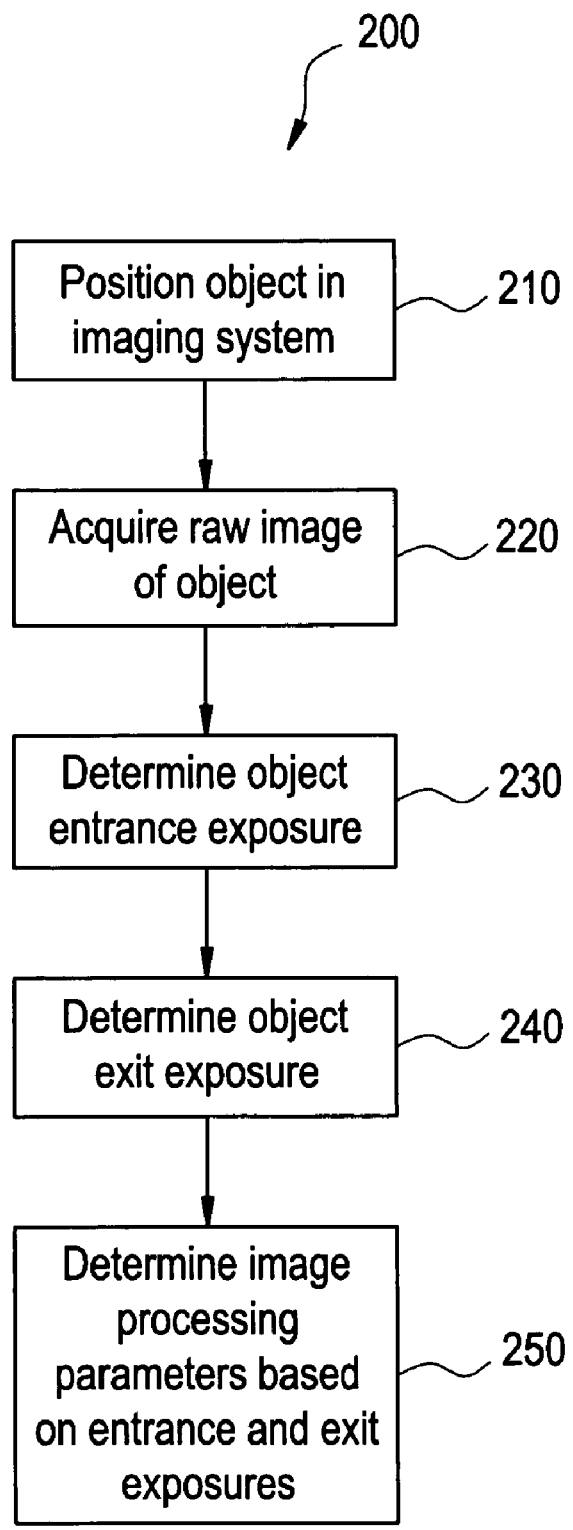
FIG. 2 illustrates a method for adaptive image processing and/or display, according to at least one embodiment of the presently described technology.

FIG. 2 illustrates a method 200 for adaptive image processing and/or display, according to at least one embodiment of the presently described technology. The method 200 includes positioning an object in an imaging system 210, acquiring a raw image of the object 220, determining an entrance exposure 230, determining an exit exposure 240, determining an image processing parameter based on the entrance and exit exposures 250.

At step 210, the object, such as a patient or selected area or anatomy of the patient, is positioned in an imaging system, such as the imaging system 100 of FIG. 1. For example, to obtain a thoracic x-ray image, a patient's chest may be positioned between an x-ray source and an x-ray detector in an x-ray system.

At step 220, a raw image of the object is acquired. For example, x-rays are transmitted from an x-ray source, through a patient or selected anatomy of the patient, and into an x-ray detector. The x-ray detector then converts the x-ray energy or radiation into a raw image. More particularly, the x-ray detector elements convert the x-ray energy or radiation into pixels of the raw image.

At step 230, an entrance exposure is determined. The entrance exposure or dose of the object includes an amount of energy or radiation, such as x-rays, that enters the object, such as a patient or selected area or anatomy of the patient. The entrance exposure or dose may be determined by one or more radiation meters or dose area product (DAP) meters, for example. The radiation or DAP meters may be positioned or located between the energy source and the object. More particularly, the radiation or DAP meters may measures the entrance exposure or dose of the object. Alternatively, the entrance exposure or dose of the object may be determined by a DAP algorithm. The DAP algorithm may estimate entrance exposure or dose based on the geometric parameters of the imaging system, such as source to image distance (SID), collimation field-of view (FOV), tube angle with respect to detector axis, and the technique parameters of the imaging system, such as exposure peak voltage (kVp), current (mA), exposure duration (msec), and spectral filtration.

At step 240, an exit exposure is determined. The exit exposure or dose of the object includes the amount of energy or radiation, such as x-rays, that exits the object, such as a patient or selected area or anatomy of the patient. The exit exposure or dose may be determined by one or more radiation meters, for example. The radiation meters may be positioned or located between the object and the energy sensor. More particularly, the radiation meters may measure the exit exposure or dose of the object.

Alternatively, the exit exposure or dose of the object may be determined by a detector exposure indicator (DEI) algorithm, for example. More particularly, the DEI algorithm may determine the detector exposure or dose based on the raw image of the object and the technique parameters of the imaging system, such as exposure peak voltage (kVp), current (mA), duration (msec), presence and properties of an antiscatter grid, spectral filtration, and detector sensitivity.

The exit exposure or dose of the image object may then be determined based on the detector exposure or dose. For example, the detector exposure or dose may be about equal to the exit exposure or dose of the imaged object. Alternatively, for example, the exit exposure or dose of the imaged object may be determined based on the detector exposure or dose and an attenuation of any materials in the path of the energy or radiation between the object and the detector. The attenuation may be a constant multiplier for all imaging techniques or a function of imaging technique parameters. For example, the detector exposure or dose may be about equal to the exit exposure or dose of a patient multiplied by the attenuation (e.g. 0.9) of a table between a detector and the patient.

The DEI algorithm may be performed by an image processor, such as the image processor 140 of FIG. 1, for example, or other such processors. Alternatively, the DEI algorithm may be performed by a device, such as a DEI processor, for example. The DEI algorithm, in particular, the steps or functions of the DEI algorithm are further discussed below with reference to FIG. 3.

At step 250, one or more image processing parameters are determined based at least in part on the entrance and exit exposures. More particularly, image processing parameters, such as spatial-domain filtering kernel sizes and weighting coefficients, frequency-domain filtering thresholds, log-subtraction parameters (dual energy only), display window-level/center adjustment parameters, and display window-width adjustment parameters, may be determined based at least in part on a ratio of exit to entrance exposures or doses (exit-to-entrance exposure ratio), for example. The exit-to-entrance exposure ratio quantifies the amount or attenuation of energy or radiation passing through an object. For example, the exit-to-entrance exposure ratio of 0 indicates that almost none of the energy or radiation passed through the object. Conversely, for example, the exit-to-entrance exposure ratio of 1 indicates that almost all of the energy or radiation passed through the object.

The amount or attenuation of energy or radiation passing through the object may be related to the object size or thickness. For example, more energy or radiation may pass through a smaller or thinner patient than a larger or thicker patient. Consequently, as the size or thickness of the object decreases, the exit-to-entrance exposure ratio increases from 0 and 1, for example. More particularly, the exit-to-entrance exposure ratio may have an inverse relationship with the size or thickness of the object. For example, a low exit-to-entrance exposure ratio (closer to 0) may correspond to a larger or thicker patient, whereas a high exit-to-entrance exposure ratio (closer to 1) may correspond to a smaller or thinner patient.

In at least one embodiment of the presently described technology, one or more lookup tables or other data references may be used to relate the entrance and exit exposures, such as the exit-to-entrance exposure ratio, to one or more corresponding image process parameters. For example, for dual energy chest exams performed using an anti-scatter grid, an exit-to-entrance exposure ratio of less than $2 \times 10^{-4}$ may correspond to log-subtraction parameter of 0.4.

Alternatively, one or more lookup tables may be used to relate entrance and exit exposures, such as the exit-to-entrance exposure ratio, to a corresponding object size or thickness. For example, an exit-to-entrance exposure ratio greater than $4 \times 10^{-4}$ may correspond to a small object, an exit-to-entrance exposure ratio between $2 \times 10^{-4}$ and $4 \times 10^{-4}$ may correspond to a medium object, and an exit-to-entrance exposure ratio of less than $2 \times 10^{-4}$ may correspond to a large object.

In at least one embodiment of the presently described technology, one or more analytical formulas may be applied to determine one or more corresponding image processing parameters, or alternatively, a corresponding object thickness or attenuation based at least in part on the entrance and exit exposures, such as the exit-to-entrance exposure ratio. For example, the log-subtraction parameter, w, for dual energy subtraction may be based upon the exit-to-entrance exposure ratio, ER, of one of the acquired image pair: $w=0.4+ER/K$, where $K=3 \times 10^{-4}$.

As described below, if the exit exposure includes a single exit exposure value, then the exit-to-entrance exposure ratio may also include a single exit-to-entrance exposure ratio value, and therefore, a single image processing parameter value, or alternatively, a single object size or thickness value. Alternatively, if the exit exposure includes a map or array of exit exposure values, then the exit-to-entrance exposure ratio may also include a map or array of exit-to-entrance exposure ratio values, and thus, a map or array of image processing parameter values, or alternatively, a map or array of object size or thickness values, each ratio value and each image processing parameter value, or alternatively, each object size or thickness value, corresponding to a location on the object, for example. Additionally, for example, the previously described maps or arrays may be referred to as spatial maps or arrays.

The entrance and exit exposures may be shown on an image display, such as the image display 150 of FIG. 1. More particularly, the attenuation of the energy or radiation passing through an object, whether a single attenuation value or a map or array of attenuation values (each attenuation value corresponding to a location on the object), may be shown on the image display, for example. Alternatively, for example, the exit-to-entrance exposure ratio, whether a single ratio value or a map or array of ratio values (each ratio value corresponding to a location on the object), may be shown on the image display. Alternatively, the image processing parameter may also be shown on the image display, whether a single image processing parameter value or a map or array of image processing parameter values (each parameter value corresponding to a location on the object), may be shown on the image display.

The step 250 of determining one or more image processing parameters may include selecting one or more new image processing parameters or adjusting one or more existing or default image processing parameters, for example. Additionally, for example, the step 250 of determining one or more image processing parameters may include not adjusting one or more existing or default image processing parameters if the existing or default image processing parameters are about equal to one or more corresponding determined image processing parameters.

As will be appreciated by those of skill in the art, certain steps may be performed in ways other than those recited above and the steps may be performed in sequences other than those recited above.

Figure 3:
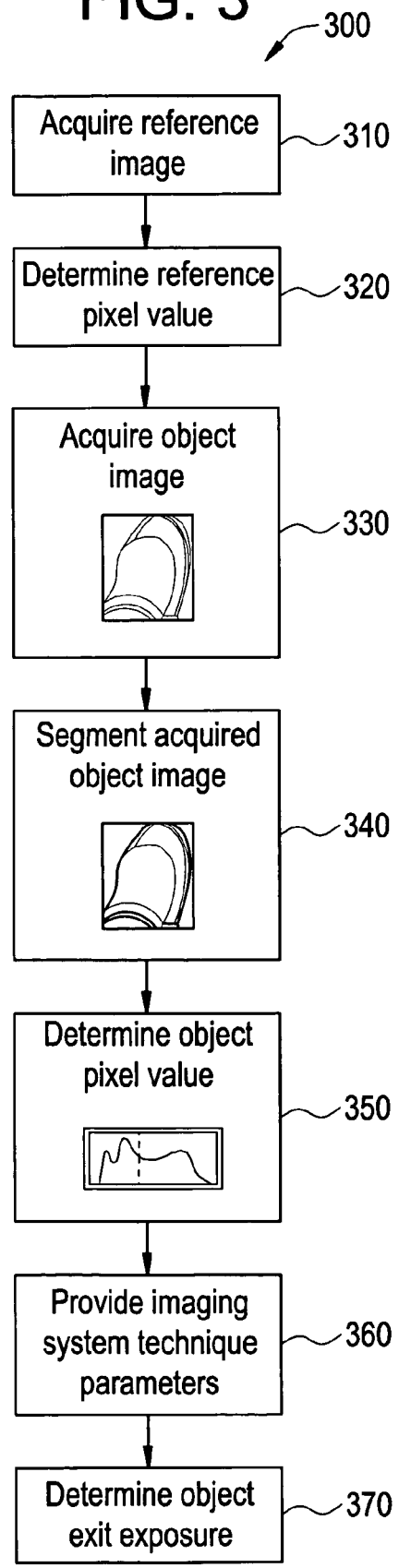
FIG. 3 illustrates a detector exposure indicator algorithm for determining the exit exposure of an imaged object, according to at least one embodiment of the presently described technology.

FIG. 3 illustrates a DEI algorithm 300 for determining the exit exposure of an imaged object, according to at least one embodiment of the presently described technology. The DEI algorithm 300 includes acquiring a reference image 310, determining a reference pixel value 320, acquiring an object image 330, segmenting the acquired object image 340, determining an object pixel value 350, providing imaging system technique parameters 360, and determining the exit exposure or dose of the object 370.

At step 310, a reference image is acquired. The reference image includes the image acquired without the object present in the imaging system. The reference image may also be referred to as a calibration image, for example.

At step 320, a reference pixel value is determined. The reference pixel value may be determined based on the reference image. More particularly, the reference pixel value includes the average or median value, for example, of the pixels in the reference image that correspond to the object, if the object were imaged. The reference pixel value may also be referred to as a calibration pixel value. The calibration pixel value establishes a relationship between image pixel values and detector exposure or dose at the technique used for calibration.

At step 330, an object image is acquired, which is described above.

At step 340, the acquired object image is segmented. The object image includes an object image area and an empty space image area. The object image area corresponds to the object on the image (i.e., the area of the image produced by energy or radiation passing through the object). Conversely, the empty space image area corresponds to the empty space on the image (i.e., the area of the image produced by energy or radiation not passing through the object). The object image area is preferably segmented. In other words, the empty space image area identified in the object image.

At step 350, an object pixel value is determined. The object pixel value may be determined based on the segmented object image. More particularly, the object pixel value includes the average or median value of all of the pixels in the segmented object image, for example. Alternatively, the object pixel value may include a map or array of the individual pixel values in the segmented image.

At step 360, technique parameters of an imaging system, such as the imaging system 100 of FIG. 1, are provided. As described above, imaging system technique parameters include exposure peak voltage (kVp), current (mA), duration (msec), presence and properties of an anti-scatter grid, spectral filtration, and detector sensitivity, for example.

At step 370, an exit exposure or dose of the imaged object is determined. A detector exposure or dose may be determined based on the reference pixel value of the reference image, the object pixel value of the segmented object image, and the technique parameters of the imaging system. The reference pixel value may be adjusted based on the technique parameters. For example, a pixel value at a calibration technique of 80 kVp may be multiplied by a factor of 2 to get a pixel value at an operative technique of 120 kVp. The detector exposure may then be determined based on the following formula: detector exposure =reference image exposure* (object pixel value/reference pixel value).

As described above, the exit exposure or dose of the image object may then be determined based on the detector exposure or dose. For example, the detector exposure or dose may be about equal to the exit exposure or dose of the imaged object. Alternatively, for example, the exit exposure or dose of the imaged object may be determined based on the detector exposure or dose and an attenuation of any materials in the path of the energy or radiation between the object and the detector. The attenuation may be a constant multiplier for all imaging techniques or a function of imaging technique parameters. For example, the detector exposure or dose may be about equal to the exit exposure or dose of a patient multiplied by the attenuation (e.g. 0.9) of a table between a detector and the patient.

If the object pixel value includes the average or median value of all of the individual pixels, then the exit exposure or dose may also include a single exit exposure or dose value for the object. Alternatively, if the object pixel value includes a map or array of the individual pixel values, then the exit exposure or dose may also include a map or array of individual exit exposure or dose values, each value corresponding to a location on the object, for example.

As will be appreciated by those of skill in the art, certain steps may be performed in ways other than those recited above and the steps may be performed in sequences other than those recited above.

The steps 210-260 of the method 200 of FIG. 2, including the steps 310-370 of the DEI algorithm 300, may be introduced into the imaging system 100 of FIG. 1 as a set of instructions on a computer-readable storage medium, such as a floppy disk or a hard drive, for example. Additionally, the set of instructions may be implemented using software, hardware, and/or firmware, for example.

While particular elements, embodiments and applications of the presently described technology have been shown and described, it is understood that the presently described technology is not limited thereto since modifications may be made by those skilled in the art, particularly in light of the foregoing teaching. It is therefore contemplated by the appended claims to cover such modifications and incorporate those features that come within the spirit and scope of the presently described technology.

The invention claimed is:

1. A method for image processing comprising:
using an imaging system to acquire a raw image of an object by passing energy through the object;
determining an entrance exposure of the imaged object, wherein the entrance exposure comprises an amount of energy that entered the imaged object when the raw image was acquired;
determining an exit exposure of the imaged object, wherein the exit exposure comprises an amount of energy that exited the imaged object when the raw image was acquired;
using an image processor to calculate a ratio of the exit exposure to the entrance exposure;
using a data source operably connected to the image processor to correlate the ratio of the exit exposure to the entrance exposure with one or more image processing parameters that can be used to enhance the acquired raw image of the object; and
at least one of:
adjusting one or more existing image processing parameters based on the correlated one or more image processing parameters,
not adjusting one or more existing image processing parameters that are about equal to the correlated one or more image processing parameters, and
selecting the correlated one or more image processing parameters that are new.

2. The method of claim 1, wherein said entrance exposure is measured with at least one dose area product meter.

3. The method of claim 1, wherein said entrance exposure is measured with at least one radiation meter.

4. The method of claim 1, wherein said exit exposure is measured with at least one radiation meter.

5. The method of claim 1, wherein said entrance exposure is determined using a dose area product algorithm that uses one or more of: a geometric parameter of the imaging system used to acquire the raw image, and a technique parameter of the imaging system used to acquire the raw image.

6. The method of claim 5, wherein the geometric parameter is one or more of: a source to image distance, a collimation field of view, and a tube angle with respect to a detector axis.

7. The method of claim 5, wherein the technique parameter is one or more of: an exposure peak voltage, a current, exposure duration, and a spectral filtration.

8. The method of claim 1, wherein said exit exposure is determined using a detector exposure indicator algorithm that uses the acquired raw image and one or more technique parameters of the imaging system used to acquire the raw image, the technique parameters including one or more of: an exposure peak voltage, a current, a duration, a property of an anti-scatter grid, a spectral filtration, and a detector sensitivity.

9. The method of claim 8, wherein the detector exposure indicator algorithm further uses a reference pixel value and an object pixel value to determine the exit exposure, the reference pixel value and the object pixel value determined by:
using the imaging system to acquire a reference image without the object present in the imaging system;
determining a reference pixel value that provides an average or median value of pixels in the reference image;
segmenting the acquired raw image to provide a segmented image of the object; and
determining an object pixel value that provides an average or median value of pixels in the segmented image of the object.

10. The method of claim 1, wherein said exit exposure includes a spatial map of exit exposure values, each value corresponding to a different location on an object.

11. The method of claim 1, wherein said one or more image processing parameters includes a spatial map of image processing parameter values, each value corresponding to a different location on an object.

12. A non-transitory computer-readable storage medium encoded with a set of instructions for a computer, said set of instructions including:
- a first routine configured to acquire a raw image of an object, the raw image being acquired by passing energy through the object;
- a second routine configured to determine an entrance dose of the imaged object, wherein the entrance dose comprises an amount of energy that entered the imaged object when the raw image was acquired;
- a third routine configured to determine an exit dose of the imaged object, wherein the exit dose comprises an amount of energy that exited the imaged object when the raw image was acquired;
- a fourth routine configured to use an image processor to calculate a ratio of the exit dose to the entrance dose;
- a fifth routine configured to correlate the ratio of the exit dose to the entrance dose with one or more image processing parameters that can be used to enhance the acquired raw image of the object; and
- a sixth routine configured to at least one of:
  - adjust one or more existing image processing parameters based on the correlated one or more image processing parameters,
  - not adjust one or more existing image processing parameters that are about equal to the correlated one or more image processing parameters, and
  - select the correlated one or more image processing parameters that are new.

13. The non-transitory computer-readable storage medium encoded with the instructions of claim 12, wherein said one or more image processing parameters is determined using a lookup table.

14. The non-transitory computer-readable storage medium encoded with the instructions of claim 12, wherein said one or more image processing parameters is determined by said ratio and a formula.

15. A system for image processing comprising:
- an imaging system configured to acquire a raw image of an object by passing energy through the object; and
- an image processor configured to receive an entrance exposure comprising an amount of energy that entered the imaged object when the raw image was acquired,
- the image processor configured to receive an exit exposure comprising an amount of energy that exited the imaged object when the raw image was acquired,
- the image processor configured to calculate a ratio of the exit exposure to the entrance exposure,
- the image processor being operably connected to a data source configured to allow the ratio of the exit exposure to the entrance exposure to be correlated with one or more image processing parameters that can be used to enhance the acquired raw image of the object, and
- the image processor configured to at least one of:
  - adjust one or more existing image processing parameters based on the correlated one or more image processing parameters,
  - not adjust one or more existing image processing parameters that are about equal to the correlated one or more image processing parameters, and
  - select the correlated one or more image processing parameters that are new.

16. The system of claim 15, further including at least one dose area product meter for determining said entrance exposure.

17. The system of claim 15, further including at least one detector exposure indicator for determining said exit exposure.

18. The system of claim 15, further including at least one radiation meter for determining said entrance exposure.

19. The system of claim 15, further including at least one radiation meter for determining said exit exposure.

20. The system of claim 15, wherein said entrance exposure is determined using a dose area product algorithm that uses one or more of: a geometric parameter of the imaging system used to acquire the raw image, and a technique parameter of the imaging system used to acquire the raw image.

21. The system of claim 20, wherein the geometric parameter is one or more of: a source to image distance, a collimation field of view, and a tube angle with respect to a detector axis, and wherein the technique parameter is one or more of: an exposure peak voltage, a current, exposure duration, and a spectral filtration.

22. The system of claim 15, wherein said exit exposure is determined using a detector exposure indicator algorithm that uses the acquired raw image and one or more technique parameters of the imaging system used to acquire the raw image, the technique parameters including one or more of: an exposure peak voltage, a current, a duration, a property of an anti-scatter grid, a spectral filtration, and a detector sensitivity.

23. The system of claim 22, wherein the detector exposure indicator algorithm further uses a reference pixel value and an object pixel value to determine the exit exposure, the reference pixel value and the object pixel value determined by:
- using the imaging system to acquire a reference image without the object present in the imaging system;
- determining a reference pixel value that provides an average or median value of pixels in the reference image;
- segmenting the acquired raw image to provide a segmented image of the object; and
- determining an object pixel value that provides an average or median value of pixels in the segmented image of the object.

* * * * *